United States Patent [19]

Gettig et al.

[11] Patent Number: 4,534,763

[45] Date of Patent: Aug. 13, 1985

[54] HYPODERMIC CARTRIDGE

[76] Inventors: William A. Gettig, Linwood, Box 417, Millheim, Pa. 16854; Gerald S. Fetterolf, P.O. Box 53, Madisonburg, Pa. 16852

[21] Appl. No.: 532,050

[22] Filed: Sep. 14, 1983

[51] Int. Cl.³ .............................................. A61M 5/00
[52] U.S. Cl. .................................. 604/239; 604/900; 128/763
[58] Field of Search ............... 604/239, 225, 900, 240, 604/241; 128/763, 764, 765

[56] References Cited

U.S. PATENT DOCUMENTS

| | | | |
|---|---|---|---|
| 950,822 | 3/1910 | McElroy | 604/272 |
| 1,331,271 | 2/1920 | MacGregor | 604/239 |
| 2,840,075 | 6/1958 | Dann et al. | 604/900 X |
| 2,855,927 | 10/1958 | Henderson | 604/241 |
| 3,330,268 | 7/1967 | Goldsmith | 128/753 |
| 3,734,095 | 5/1973 | Santomieri | 604/900 X |
| 3,753,432 | 8/1973 | Guerra | 128/764 |
| 4,186,750 | 2/1980 | Patel | 128/748 |

FOREIGN PATENT DOCUMENTS 1002348  8/1965  United Kingdom .............. 604/241

*Primary Examiner*—John D. Yasko

[57] ABSTRACT

A hypodermic cartridge includes a barrel having a cannula attached to a forward end thereof. The rear or inner end of the cannula extends into the barrel interior and is provided with a deflected or bent section having its distal portion juxtaposed the peripheral wall of the barrel. In use, upon aspiration, the first droplet of blood is readily viewable through the barrel wall regardless of whether the medicament contained in the barrel is clear, translucent or opaque.

10 Claims, 3 Drawing Figures

HYPODERMIC CARTRIDGE

This invention relates generally to hypodermic cartridges or syringes and more particularly to an improved construction more accurately signalling blood upon aspiration.

As well known to medical personnel, medications adapted to be administered by means of injection, such as through a needle or cannula, are designed for introduction into the patient's system in a specific manner. Certain medications must not be injected into a patient's vein or artery but instead, are intended to be applied intramuscularly or subcutaneously and vice versa. When such a medication is administered it is the practice for the nurse or physician to aspirate the injection device after insertion of the cannula while observing the area of the inner or rear end of the cannula where it communicates with the forward portion of the transparent glass or plastic barrel of the hypodermic apparatus. If the forward point of the cannula has penetrated a vein or artery, blood will immediately appear in that area. With many hypodermic devices and medications, the foregoing procedure presents no problem or little difficulty in the detection of blood upon aspiration. However, with certain medications such as those comprising a translucent or opaque medicament, visual detection of the presence of blood presents somewhat of a problem or at least an inconvenience since an excessive amount of blood must be withdrawn through the cannula before it becomes visible at the lateral periphery of the applicator barrel or cartridge, in the area immediately behind the needle hub.

An earlier example of an apparatus constructed to provide visual observation of blood upon aspiration will be found in U.S. Pat. No. 4,240,423 issued Dec. 23, 1980 to Akhavi. The referenced patent provides visual detection of blood at the inner end of a hypodermic needle by constructing the needle hub of a transparent plastics material. With the present invention, a construction is provided whereby upon aspiration, blood is immediately detected at the very distal portion of the inner end of a hypodermic needle even when the contained medicament is translucent or opaque and without the necessity of providing a transparent needle hub. Additionally, this detection is possible instantaneously upon existence of the first droplet of blood at the distal portion of the needle inner end.

The instant invention proposes an improved construction for a hypodermic cartridge wherein the inner end of the cannula extends rearwardly through the nose of a cartridge barrel into the forward portion of its interior with this inner end being bent at a pronounced angle such that the distal open end thereof is juxtaposed the inner surface of the wall or periphery of the barrel. In this manner, upon aspiration, the initial droplet of blood which appears at this distal end portion will be juxtaposed the transparent wall of the cartridge barrel and will be readily viewable by the user of the device regardless of the opacity or viscosity of the contained medicament.

Accordingly, one of the objects of the present invention is to provide an improved hypodermic cartridge having a cannula with its inner end disposed within the interior of the cartridge barrel and juxtaposed the inner surface of the barrel wall.

A further object of the present invention is to provide an improved hypodermic cartridge including a transparent barrel having a cannula fixedly attached to the nose thereof with its inner end projecting into the interior of the barrel and disposed at an angle of between 100°–130° relative the axially extending portion of the cannula.

An additional object of the present invention is to provide an improved hypodermic cartridge including a transparent barrel provided with a cannula having an inner end projecting into the interior of the barrel with this inner end angularly disposed adjacent the barrel forward end wall and having a substantially square cut distal portion juxtaposed the inner surface of the barrel side wall.

With these and other objects in view which will more readily appear as the nature of the invention is better understood, the invention consists in the novel construction, combination and arrangement of parts hereinafter more fully described, illustrated and claimed.

A preferred and practical embodiment of the invention is shown in the accompanying drawing, in which.

Similar reference characters designate corresponding parts throughout the several figures of the drawing.

Figure 1:
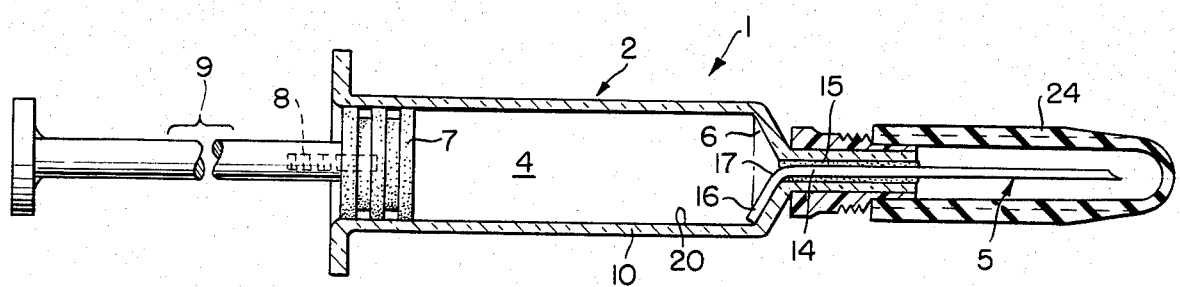
FIG. 1 is a longitudinal sectional view illustrating the hypodermic cartridge of the present invention.

Referring now to the drawing, particularly FIG. 1, the present invention will be seen to relate to a hypodermic cartridge or syringe generally designated 1, including an elongated cylindrical body or barrel 2 constructed of suitable transparent material such as glass or plastic. A rear open end 3 is provided for the filling of the interior 4 of the barrel with the desired medicament M and thereafter, appropriate force-transmitting means for urging the medicament through the opposite end of the barrel 2. Such force-transmitting means is secondary to the present invention which is directed primarily to the construction of the needle or cannula 5 adjacent the forward end wall 6 of the barrel. As shown in FIG. 1, a suitable plug or piston 7 may be inserted through the barrel rear open end 3 and which carries a threaded stud 8 projecting from its rear wall for the reception of a suitable plunger actuating rod 9.

As shown in the drawing, the forward end wall 6 of the barrel is preferably slightly tapered or inclined away from the adjacent lateral or peripheral wall 10 of the barrel and leads to a central axially disposed bore 11 extending forwardly through the cone or nose 12 of the barrel.

The cannula 5 includes a straight or axially extending main section 13 projecting well forward of the end of the barrel nose 12 and the rear portion 14 of this straight cannula section will be understood to be fixedly attached to the nose of the barrel by means of any suitable adhesive 15 which serves not only to securely attach the cannula to the barrel but also provides a fluid-tight seal. As shown most clearly in FIGS. 1 and 2 of the drawing, the rear portion of the cannula 5 does not terminate at the end of the barrel bore 11 but instead projects rearwardly thereof and is formed as a bent inner end 16 fully disposed within the interior 4 of the barrel. The juncture 17 between the bent end 16 and the remaining straight axially disposed portion 13-14 of the cannula will be seen to be formed as a smoothly curved section so as not to restrict the interior bore or passageway 18 of the cannula. The inner end 16 itself may be slightly curved or substantially straight and in either case, this inner end 16 will be understood to be disposed at an angle of 100°-130° relative the remainder or axially extending portion 13-14 of the cannula.

The bent inner end 16 is closely disposed relative the tapered or angular forward end wall 6 of the barrel and may be flushly disposed thereagainst. Such a disposition, of course, would occur if the inclination of the inner end 16 and the end wall 6 coincided although it will be appreciated that the operation of the present invention does not require an exact coincidence between these two components. An important feature however, resides in the disposition of the distal portion 19 of the cannula inner end 16 which will be seen to be juxtaposed the inner surface 20 of the barrel peripheral wall 10 in an area immediately adjacent the barrel forward wall 6. It is this juxtaposition that insures ready visual detection of blood upon aspiration with the present hypodermic cartridge since the first droplet of blood to appear at the distal portion 19 impinges the inner surface 20 of the transparent barrel wall 10 and thus is immediately detected, regardless of the viscosity or opacity of the medicament M contained therein.

To preclude any impeding of the transmission of fluid, in either direction, through the passageway 18 of the cannula, the distal portion 19 is preferably square cut relative its adjacent inner end 16 such that only one edge of distal portion 16 is juxtaposed the barrel peripheral wall 10. Quite obviously, it will be that portion of the edge closest to the barrel wall 10 that will be engaged with or juxtaposed the barrel inner surface.

Figure 2:
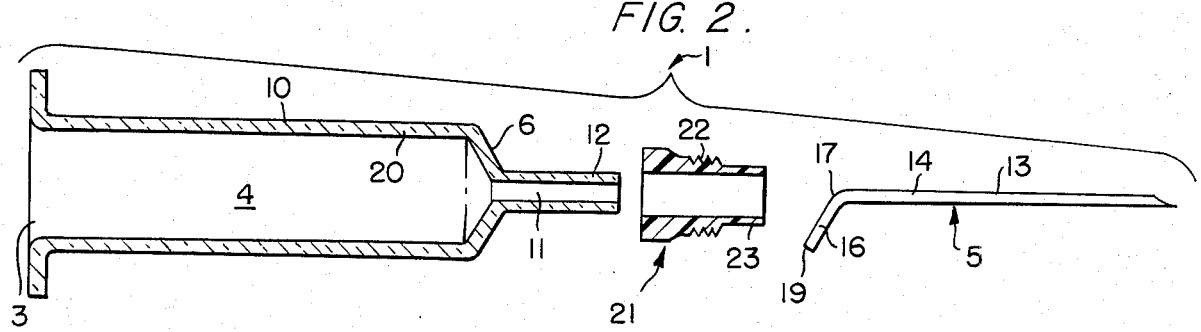
FIG. 2 is an exploded side elevation of the structure of FIG. 1.

As shown in FIGS. 1 and 2 of the drawing, a hub or ferrule 21 cooperates with the barrel nose 12 and cannula 5 to enhance the attachment of these two latter components. Details of a typical ferrule useable with the present invention will be found in my prior U.S. Pat. No. 3,247,850 issued Apr. 26, 1966. The instant ferrule 21 will be understood to be suitably secured to both the barrel nose 12 and cannula 5 such as by the same previously mentioned adhesive 15 retaining the cannula within the nose bore 11. External threads 22 provide ready means for the removable attachment of a suitable substantially rigid cap (not shown) while the elongated forward extension 23 is adapted to receive and retain a flexible, resilient protective sleeve 24 as shown in FIG. 1.

Figure 3:
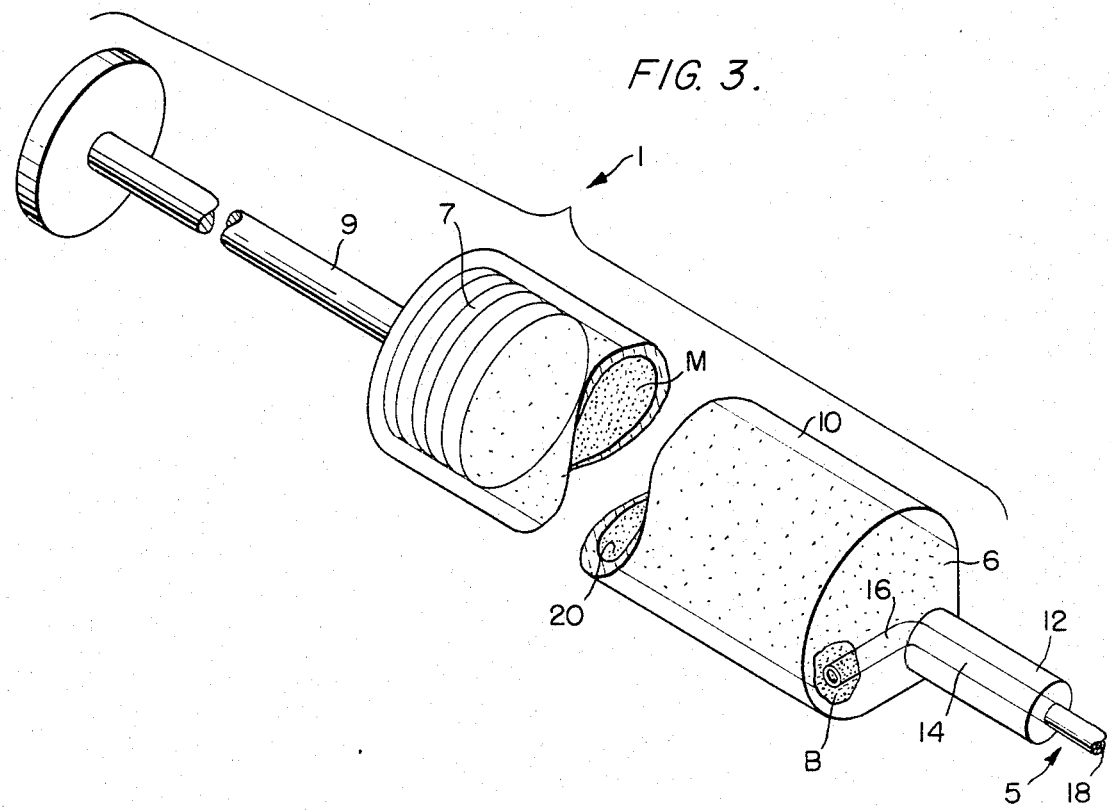
FIG. 3 is a partial front perspective view of the present invention, illustrating its operation upon aspiration.

With the foregoing construction in mind, it will be appreciated that even with an opaque or sediment-type medicament M contained within the barrel 2, such as shown in FIG. 3, upon aspiration of the present hypodermic cartridge the first droplet of blood B to appear at the distal portion 19 of the cannula 5 will be instantaneously visible to the user through the transparent material of the barrel wall 10. In view of the proximity of the bent inner end 16 to the barrel tapered forward wall 6 and the juxtaposition of the distal portion 19 thereof with the barrel peripheral wall 10, it will be appreciated that detection of blood upon aspiration is not thwarted by the use of any type of medicament. The referenced disposition of the inner end 16 and its distal portion 19 insures ready visibility of at least the distal portion 19 even with an opaque medicament M and the very first droplet of blood to appear upon aspiration will be understood to errode any sediment-type medicament such that its presence is instantly detected.

We claim:

1. A hypodermic cartridge including, a barrel provided with a peripheral wall defining an interior adapted to contain a medicament, said peripheral wall including an inner surface, a forward end wall communicating with a nose projecting forward of said end wall, said nose having a bore communicating with said barrel interior, a cannula provided with a central passageway, said cannula including a substantially straight main section having a rear portion disposed in said nose bore, said cannula having an inner end projecting from said rear portion into said barrel interior, said cannula inner end angularly deflected toward said barrel peripheral wall to provide a bent inner end, said forward end wall tapered from said barrel peripheral wall to said bore of said nose, said cannula bent inner end disposed at an angle substantially coinciding with that of said forward end wall and flushly engaging same throughout its extent, said bent inner end provided with a distal portion juxtaposed said barrel inner surface, and said cannula distal portion juxtaposed the intersection of said barrel peripheral wall and forward end wall whereby, upon aspiration blood is readily visually detected at said cannula distal portion through said barrel wall.

2. A hypodermic cartridge according to claim 1 wherein, said cannula inner end is bent 100°-130° relative the longitudinal axis of said barrel and cannula rear portion.

3. A hypodermic cartridge according to claim 1 wherein, said cannula distal portion is substantially square cut relative the axial extent of the adjacent said inner end whereby flush contact between all of said distal portion and said barrel inner surface is precluded.

4. A hypodermic cartridge according to claim 1 including, a ferrule on said nose, said cannula extending through said ferrule, and means securing said cannula rear portion and ferrule to said nose.

5. A hypodermic cartridge according to claim 1 wherein, said medicament is opaque.

6. A hypodermic cartridge according to claim 1 wherein, said medicament is translucent.

7. A hypodermic cartridge according to claim 1 wherein, said medicament is clear.

8. A hypodermic cartridge according to claim 2 wherein, said inner end is bent 120°.

9. A hypodermic cartridge according to claim 4 including, a protective sleeve removably attached to said ferrule.

10. A hypodermic cartridge according to claim 9 wherein, said sleeve is resilient and frictionally attached to said ferrule.

* * * * *